(12) United States Patent
Liu et al.

(10) Patent No.: US 9,901,440 B2
(45) Date of Patent: Feb. 27, 2018

(54) BREAST PROSTHESIS SUPPORT DEVICE BASED ON TISSUE MATRIX MATERIAL, AND PREPARATION METHOD THEREFOR

(71) Applicant: Beijing Ruijian Gaoke Biotechnology Co., Ltd., Beijing (CN)

(72) Inventors: Zhi-gang Liu, Beijing (CN); Xinhua Liu, Beijing (CN)

(73) Assignee: Beijing Ruijian Gaoke Biotechnology Co., Ltd., Beijing (CN)

( * ) Notice: Subject to any disclaimer, the term of this patent is extended or adjusted under 35 U.S.C. 154(b) by 11 days.

(21) Appl. No.: 14/911,497

(22) PCT Filed: May 29, 2014

(86) PCT No.: PCT/CN2014/078744
§ 371 (c)(1),
(2) Date: Feb. 11, 2016

(87) PCT Pub. No.: WO2015/021807
PCT Pub. Date: Feb. 19, 2015

(65) Prior Publication Data
US 2016/0199173 A1    Jul. 14, 2016

(30) Foreign Application Priority Data

Aug. 14, 2013 (CN) .......................... 2013 1 0352373

(51) Int. Cl.
*A61F 2/12* (2006.01)
*A61L 27/36* (2006.01)

(52) U.S. Cl.
CPC ............ *A61F 2/12* (2013.01); *A61L 27/3641* (2013.01); *A61F 2230/0095* (2013.01); *A61F 2240/001* (2013.01); *A61L 2430/04* (2013.01)

(58) Field of Classification Search
CPC ....................................................... A61F 2/12
(Continued)

(56) References Cited

U.S. PATENT DOCUMENTS 6,616,685 B2 * 9/2003 Rousseau .............. A61F 2/0063
                                                                606/151
8,758,447 B2 * 6/2014 Shetty .................... A61L 27/18
                                                                623/23.65
(Continued)

FOREIGN PATENT DOCUMENTS

CN         101480360 A      7/2009
CN         102470032 A      5/2012
(Continued)

OTHER PUBLICATIONS

International Search Report of PCT/CN2014/078744, dated Sep. 2, 2014.
(Continued)

*Primary Examiner* — Suzette J Gherbi
(74) *Attorney, Agent, or Firm* — Banner & Witcoff, Ltd.

(57) ABSTRACT

The present invention relates to a support device for breast prosthesis based on an acellular matrix material of a biological tissue. The support device for breast prosthesis is formed by tailoring a membranaceous material into a petal-shaped planar biological matrix blank and by connecting adjacent edges thereof. The support device can match with the breast prosthesis; and provide a support, fixation and coverage for the breast prosthesis in various surgical operations such as mammoplasty and breast orthopedics, to avoid the ptosis and translocation of the breast prosthesis, thereby achieving desirable effects of plastic surgery. Once being implanted, the matrix material of a biological tissue can be integrated into the surrounding breast tissue of the subject, and thus transformed into new tissues in human body without the retention of foreign bodies. The present invention further relates to a method for manufacturing a support device, and a membranaceous biological matrix material.

18 Claims, 5 Drawing Sheets

(58) Field of Classification Search
USPC .......................................................... 623/7–8
See application file for complete search history.

(56) References Cited

U.S. PATENT DOCUMENTS

| | | | |
|---|---|---|---|
| 2005/0228487 A1* | 10/2005 | Kujawski | A61F 2/06 623/1.26 |
| 2006/0030939 A1 | 2/2006 | Frank | |
| 2007/0088434 A1 | 4/2007 | Frank | |
| 2007/0276507 A1* | 11/2007 | Bertram | A61F 2/042 623/23.65 |
| 2008/0281419 A1 | 11/2008 | Matheny et al. | |
| 2010/0028396 A1 | 2/2010 | Ward et al. | |
| 2010/0131075 A1* | 5/2010 | Ludlow | A61L 27/18 623/23.66 |
| 2011/0022171 A1 | 1/2011 | Richter et al. | |
| 2011/0035004 A1 | 2/2011 | Maxwell | |
| 2011/0224800 A1* | 9/2011 | Ludlow | A61L 27/3804 623/23.65 |
| 2012/0010728 A1* | 1/2012 | Sun | A61L 27/50 623/23.72 |
| 2013/0158658 A1* | 6/2013 | Hayzlett | A61F 2/02 623/8 |
| 2014/0128891 A1* | 5/2014 | Astani-Matthies | A61F 2/0063 606/151 |
| 2015/0150674 A1* | 6/2015 | Ansorge | A61F 2/12 623/8 |
| 2015/0351891 A1* | 12/2015 | Moses | A61F 2/12 623/8 |
| 2016/0000551 A1* | 1/2016 | Khouri | A61F 13/145 623/23.7 |

FOREIGN PATENT DOCUMENTS

| | | |
|---|---|---|
| CN | 103068413 A | 4/2013 |
| CN | 103108661 A | 5/2013 |
| CN | 103393482 A | 11/2013 |
| CN | 203447388 U | 2/2014 |
| EP | 0230672 A2 | 8/1987 |
| JP | 2008508956 A | 3/2008 |
| JP | 2011529375 A | 12/2011 |
| WO | 2012149253 A1 | 11/2012 |
| WO | 2014041577 A1 | 3/2014 |

OTHER PUBLICATIONS

Third Party Observation for Application No. EP20140836791, dated Feb. 16, 2017, 23 pages.

Evaluation of a novel Breast Reconstruction Technique Using the Braxon Accellular Dermal Matrix: A New Muscle-Sparing Breast Reconstruction, AnzjSurg.com, 2014, 6 pages.

Office for Harmonisation in the Internal Market, Confirmation of application for community design, dated May 22, 2013, 4 pages.

Supplementary European Search Report of EP 14836791, dated May 29, 2017.

* cited by examiner

BREAST PROSTHESIS SUPPORT DEVICE BASED ON TISSUE MATRIX MATERIAL, AND PREPARATION METHOD THEREFOR

TECHNICAL FIELD

The present invention relates to the field of plastic surgery, and in particular, to an implantable biological device for fixation, support and coverage of the breast prosthesis in various surgical operations such as female breast augmentation, breast reconstruction, mammoplasty and breast orthopedics. The invention also relates to a method to manufacture the device.

BACKGROUND OF THE RELATED ART

Female breast augmentation, breast reconstruction, mammoplasty and breast orthopedics are widely used in patients with breast cancer after surgical resection and people in need of plasty. During the past 20 years, such surgery techniques have been improved greatly. The probability of complications occurring within a short period after the surgery has been significantly decreased. The breast prosthesis has achieved widespread application in breast augmentation and breast reconstruction. However, performing breast augmentation, breast reconstruction, mammoplasty and breast orthopedics by using breast prosthesis could still cause many serious problems during a longer period after the surgery. These problems include the sclerosis of fibrous (scar) tissue encapsulating the prosthesis and the breast distortion, resulting in undesirable aesthetic effects as well as the problems such as discomfort, mastosis and the like. The sclerosis and contraction of the capsule may rupture the aged breast prosthesis over time. Similar problems may occur in about one out of six patients implanted with breast prosthesis.

The fixation and support of the breast prosthesis mainly depend on autologous tissues of the patient. Due to the gravity of the breast prosthesis and the relaxation of the human tissue, the breast prosthesis may further prolapse or translocate over time and thereby directly affect the aesthetic effect. For patients with the breast resected, the difficulty for breast reconstruction increases due to the lack of support from autologous surrounding tissues of the patients. Autologous breast reconstruction is also referred to the operation of moving the skin, fat or muscle of other autologous regions to the breast of the patients. The tissue required by autologous reconstruction may be collected from abdomen, upper back, upper hip or hip. This type of surgery increases the complexity of surgery. It could introduce additional donor site wounds and damages during tissue collection and result in a longer recovery time and the formation of extra scars. In addition, autologous reconstruction is not suitable for overweighed and smoking patients, and patients with surgical history or circulatory system diseases in the tissue collection region. Furthermore, it is difficult for lean patients to use this method in breast reconstruction since there are insufficient soft tissues in abdomen and back.

Tissue matrices made from donated human cadaver tissues or from the properly processed animal tissues began to be utilized in recent few years in various surgical operations such as female breast augmentation, breast reconstruction, mammoplasty and breast orthopedics. Since these tissue materials are generally sheet-like or planar membranaceous materials, during the breast reconstruction surgery, surgeons need to tailor the materials into the shapes and sizes according to the situation of surgeries and implants used. The irregular shapes and sizes of the tissue matrices made by the surgeon during surgical operations often do not fit well to the selected breast prosthesis and the surgical region of a patient, resulting in less desirable plastic and cosmetic effect. For example, it is difficult to avoid folding or pleating, to manage the shape of the breast and to achieve a proper projection of the reconstructed breast. Meanwhile, since the materials are expensive and the operations are also error prone for the surgeons to tailor the materials into shapes on the spot via visual inspection when performing the surgeries, the materials could be wasted that increases the surgical costs.

Therefore, implantable tissue matrix devices for facilitating the fixation, support and coverage of the breast prosthesis in female breast augmentation, breast reconstruction, mammoplasty and breast orthopedics needs to be further developed and improved.

CONTENT OF THE INVENTION

The present invention relates to the design and the manufacturing methods of several kinds of biological device based on an acellular tissue matrix material. They provide the supporting, fixing and covering materials for the breast prosthesis in various surgical operations such as mammoplasty and breast orthopedics, enabling the doctors to avoid the tailoring of the materials into shapes on the spot during the surgery and therefore to reduce the operation time. In addition, the ptosis and translocation of the breast prosthesis after reconstruction could be avoided so that better plastic and cosmetic effects may be achieved.

The first aspect of the present invention proposes a support device for brat prosthesis based on an acellular matrix of a biological tissue and a method for manufacturing the device. This is accomplished by the following technical solutions:

a support device for breast prosthesis based on a tissue matrix material, comprising a petal-shaped planar biological matrix blank tailored from a membranaceous biological planar material, wherein adjacent edges of the petal-shaped planar biological matrix blank are connected to form the support device for breast prosthesis.

In one embodiment the membranaceous biological planar material is an acellular tissue matrix material.

In one embodiment, the number of the petal-shaped planar biological matrix blanks is 2-5.

In one embodiment, the support device for breast prosthesis is a support device having bowl-shaped or cup-shaped curved surfaces.

In one embodiment, the petal-shaped planar biological matrix blanks comprise at least one drainage hole.

In one embodiment, the drainage holes are provided in the middle of the connected petal-shaped planar biological matrix blank.

In one embodiment, the drainage holes are of a single rounded, square, rectangular or triangular shape, or a combination of a plurality of shapes.

In one embodiment, each of the petal-shaped planar biological matrix blanks has three convex edges.

In one embodiment, wherein a support device having bowl-shaped or cup-shaped curved surfaces is constructed by stitching, adhering, laser-welding or radiofrequency-welding of the adjacent convex edges between two adjacent petal-shaped planar biological matrix blanks together.

In one embodiment, wherein the membranaceous biological planar material has a length of 10-25 cm, and a width of 6.25 cm.

In one embodiment, the pore size of the drainage holes is 2-6 mm.

The second aspect of this invention presents a method for manufacturing the support device described above for breast prosthesis based on the tissue matrix material, the method comprising the steps of:

(a) providing a skin tissue, small intestine submucosa, diaphragm, muscle tendon or bladder as a raw material, that is collected from a donated human cadaver or from an animal;

(b) performing the decellularization, virus inactivation and sterilization of the raw material in step (a), to produce a membranaceous planar matrix material; or reconstructing from the homogenized tissue matrix and/or extracted collagen after performing the decellularization, virus inactivation and sterilization of the raw material in step (a), to form membranaceous planar matrix material;

(c) tailoring the membranaceous planar matrix material obtained from step (b) to form a petal-shaped planar biological matrix blank;

(d) connecting adjacent edges of the petal-shaped planar biological matrix blank in step (c) to form the support device for breast prosthesis.

In one embodiment, the number of the petal-shaped planar biological matrix blanks is 2-5.

In one embodiment, the support device for breast prosthesis is a support device having bowl-shaped or cup-shaped curved surfaces.

In one embodiment, the petal-shaped planar biological matrix blanks comprise at least one drainage hole.

In one embodiment, the drainage holes are provided in the middle of the connected petal-shaped planar biological matrix blank.

In one embodiment, the drainage holes are of a single rounded, square, rectangular or triangular shape, or a combination of a plurality of shapes.

In one embodiment, each of the petal-shaped planar biological matrix blanks has three convex edges.

In one embodiment, wherein, a support device having bowl-shaped or cup-shaped curved surfaces is formed by stitching, adhering, laser-welding or radiofrequency-welding of the adjacent convex edges of two adjacent petal-shaped planar biological matrix blank together.

In one embodiment, wherein, the membranaceous biological planar material has a length of 10-25 cm, and a width of 25 cm.

In one embodiment, the pore size of the drainage holes is 2-6 mm.

The third aspect of this invention provides a membranaceous biological matrix material which is based on the membranaceous planar matrix material obtained in step (b) of the method according to the second aspect of the present invention.

By implementing the technical solution described in the above three aspects, the present invention provides a support, fixation and coverage for the breast prosthesis in various surgical operations such as mammoplasty and breast orthopedics, thereby avoids the tailoring of the materials into shapes on the spot by surgeons during the surgery, and educes the operation time. Meanwhile, the support device of the embodiments of the present invention can match with the breast prosthesis to avoid the ptosis and translocation of the breast prosthesis. Once being implanted, the matrix material of the biological tissues can be integrated into the surrounding breast tissues and transformed into new tissues in the human body without the residues of foreign bodies, thereby achieving ideal plastic and cosmetic effects.

DESCRIPTION OF THE DRAWINGS

FIG. 1b is a support device for breast prosthesis having bowl-shaped or cup-shaped curved surfaces, which is constructed by stitching with the tailored design of the two petal-shaped planar tissue material in FIG. 1a;

FIG. 2b is a support device for breast prosthesis having bowl-shaped or cup-shaped curved surfaces, which is constructed by stitching with the tailored design of the three petal-shaped planar tissue material in FIG. 2a;

FIG. 3b is a support device for breast prosthesis having bowl-shaped or cup-shaped curved surfaces, which is constructed by stitching with the tailored design of the four petal-shaped planar tissue material in FIG. 3a;

FIG. 4b is a support device for breast prosthesis having bowl-shaped or cup-shaped curved surfaces, which is constructed by stitching with the tailored design of the five petal-shaped planar tissue material in FIG. 4a;

DETAILED DESCRIPTION OF EMBODIMENTS

Hereinafter, the present invention may be further illustrated in detail with reference to accompanying drawings and specific examples.

The following examples are merely used to illustrate the technical solutions of the present invention more clearly, rather than hereby to limit the protection scope of the present invention.

The embodiments of the present invention proposes a biological tissue device having bowl-shaped or cup-shaped curved surfaces, which is produced by tailoring and stitching or adhering an acellular tissue matrix material via a specific 2-5 petal-shaped design, see FIG. 1 to FIG. 4, wherein the shape of more than 5 petals may also be used to form a biological tissue support device having bowl-shaped or cup-shaped curved surfaces with different specifications, in order to match with the breast prosthesis with various specifications.

The embodiments of the present invention may also be a planar biological device produced by tailoring a sheet material via a specific 2-5 (or more than 5) petal-shaped design. The planar biological device is stitched or adhered to a bowl-shaped or cup-shaped device matching with the breast prosthesis with various specifications before use.

The middle part connected between each specific petal-shaped design is provided with a plurality of drainage holes, to facilitate the rapid removal of the postoperative fluid. The pore size of drainage holes is between 2~6 mm, and can comprise various shapes, such as a rounded, square, rectangular or triangular shape, and the like, and can further comprise a plurality of different shapes at the same time. The drainage holes can also be disposed in other positions of the petals, and there may be different combination modes for the arrangement of size, number and position of the drainage holes.

In one specific embodiment, each petal of all petal-shaped designs has three convex edges, and the adjacent convex edges of two petals can be stitched or adhered together to form a curved surface. The size of the petals and the curvature of the convex edges may vary depending on the following factors: the number of the petals specifically as designed, the shape and specification of the breast prosthesis to be matched, and the mode and extent of covering the breast prosthesis.

In one specific embodiment, the adjacent convex edges between petals can be stitched or adhered together by various methods, and both permanent surgical sutures and degradable surgical sutures can be used. Further, both a single-needle suture method and a continuous suture method can be used. They can be adhered. Adhesion can be performed with various commonly used tissue adhesives (glues), and can also be welded by laser or radiofrequency energy.

Figure 1A:
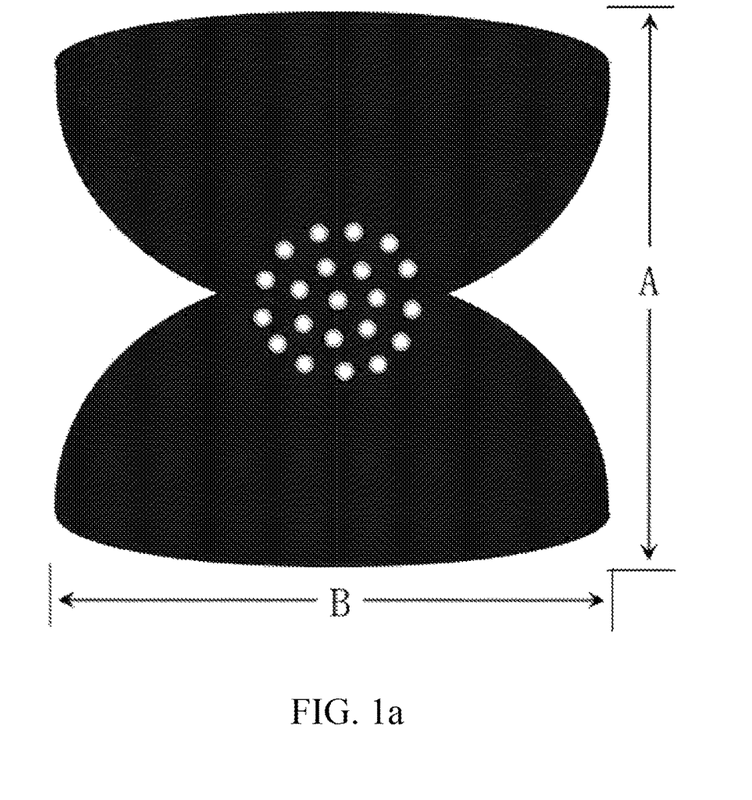
FIG. 1a is a tailored design of a two petal-shaped planar tissue material.
Figure 1B:
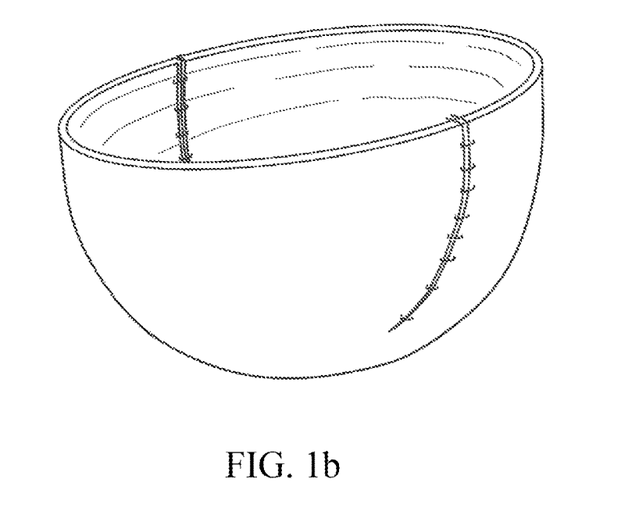

FIG. 1a shows a two-petal-shaped specific design of one embodiment of the present invention, using a rectangular tissue matrix having a length A of 10-25 cm, a width B of 6~20 cm and a thickness of 0.5~2.0 mm. The tissue matrix is tailored into two petals having a width of 6~18 cm and a height of 5~12 cm. After the adjacent convex edges between the petals being stitched or adhered together, a biological tissue bowl cover or cup cover having a caliber of 5~15 cm and a height of 4~10 cm is formed (see FIG. 1b), and can support breast prosthesis at sizes between 125 cc and 1250 cc.

Figure 2A:
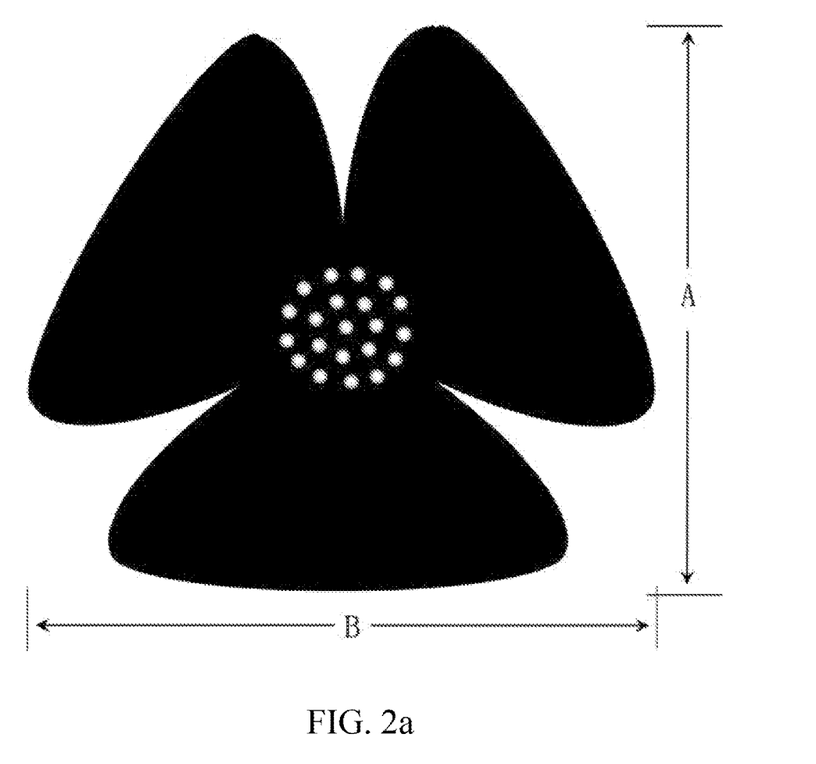
FIG. 2a is a tailored design of a three petal-shaped planar tissue material.
Figure 2B:
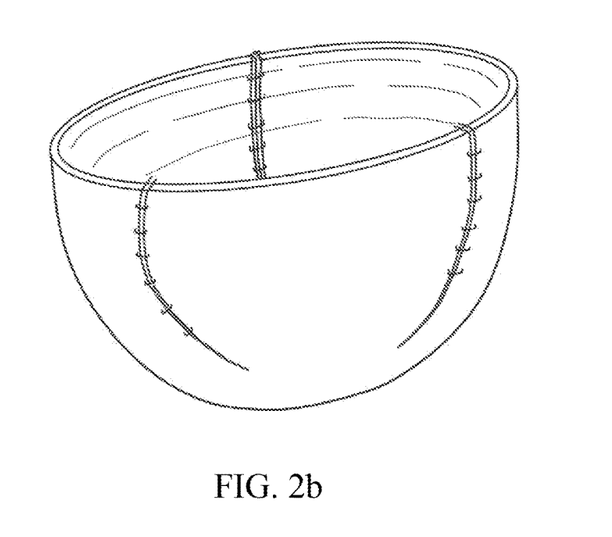

FIG. 2a shows a three-petal-shaped specific design of one embodiment of the present invention, using a square tissue matrix having a length A of 10~25 cm, a width B of 10~25 cm and a thickness of 0.5~2.0 mm. The tissue matrix is tailored into three petals having a width of 6~20 cm and a height of 5~18 cm. After the adjacent convex edges between the petals being stitched or adhered together, a biological tissue bowl cover or cup cover having a caliber of 5~15 cm and a height of 4~10 cm is formed (see FIG. 2b), and can support breast prosthesis at sizes between 125 cc and 1250 cc.

Figure 3A:
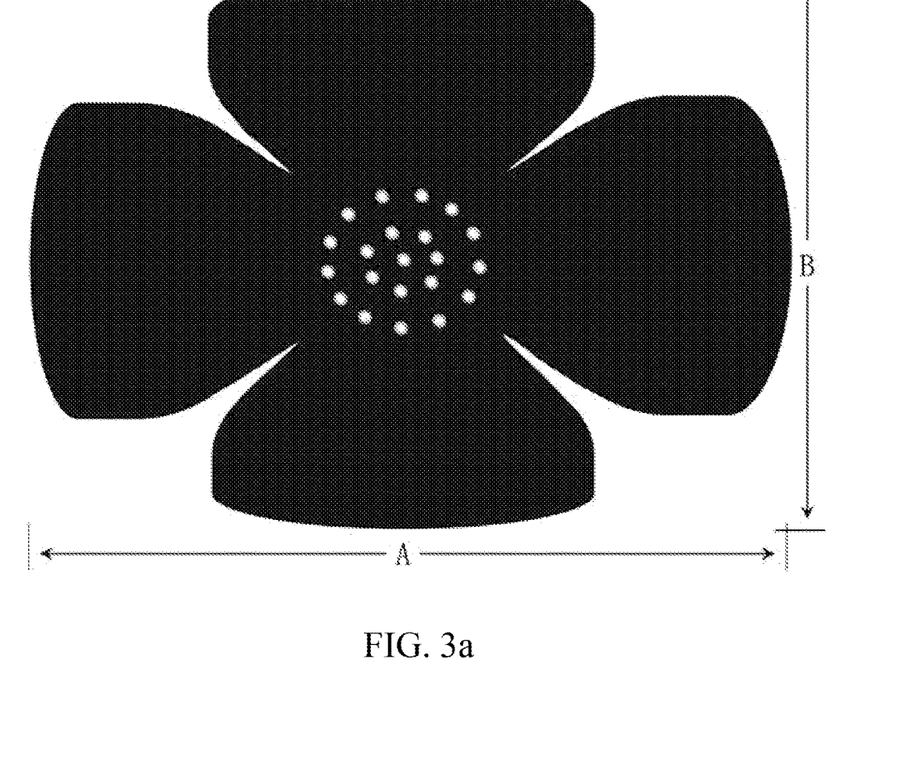
FIG. 3a is a tailored design of a four petal-shaped planar tissue material.
Figure 3B:
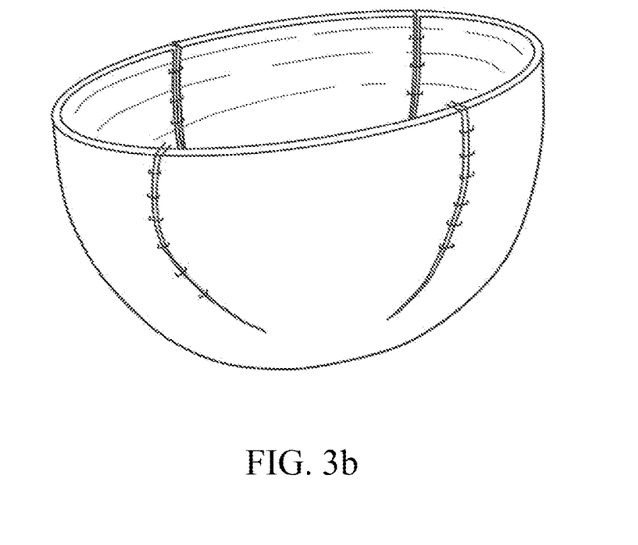

FIG. 3a shows a four-petal-shaped specific design of one embodiment of the present invention, using a rectangular tissue matrix having a length A of 10~25 cm, a width B of 8~20 cm and a thickness of 0.5~2.0 mm. The tissue matrix is tailored into two kinds of petals having different sizes and shapes, in which two petals have a width of 6~12 cm and a height of 4~10 cm, and the other two petals have a width of 5~10 cm and a height of 5~12 cm. After the adjacent convex edges between the petals being stitched or adhered together, a biological tissue bowl cover or cup cover having a caliber of 5~15 cm and a height of 4~10 cm is formed (see FIG. 3b), and can support breast prosthesis at sizes between 125 cc and 1250 cc. In addition, the four-petal-shaped specific design of another embodiment of the present invention can also use a square tissue matrix having a length A of 10~25 cm, a width B of 10~25 cm and a thickness of 0.5~2.0 mm. The tissue matrix is tailored into four identical petals having a width of 5~12 cm and a height of 5~12 cm.

Figure 4A:
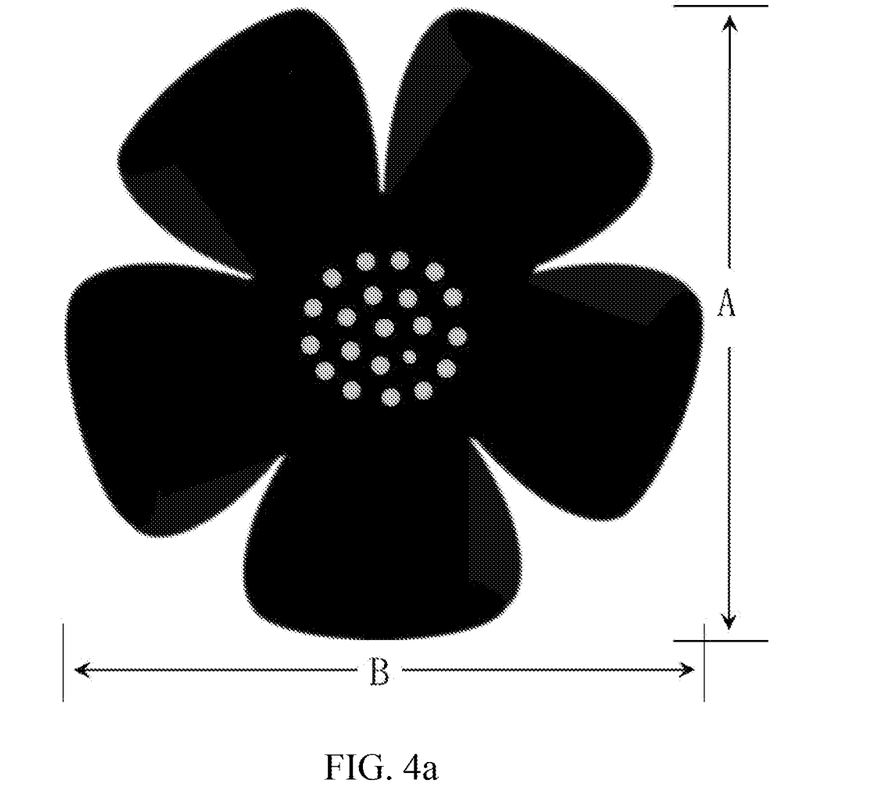
FIG. 4a is a tailored design of a five petal-shaped planar tissue material.
Figure 4B:
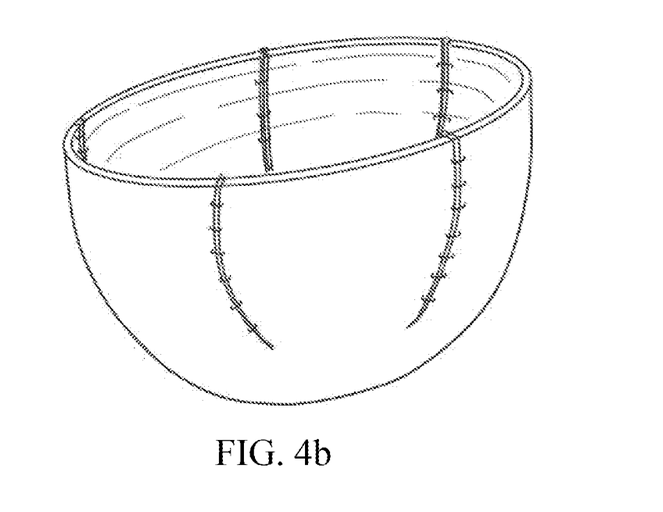

FIG. 4a shows a five-petal-shaped specific design of one embodiment of the present invention, using a square tissue matrix having a length A of 10~25 cm, a width B of 15~25 cm and a thickness of 0.5~2.0 mm which is tailored into five identical petals having a width of 5~11 cm and a height of 4~10 cm. After the adjacent convex edges between the petals being stitched or adhered together, a biological tissue bowl cover or cup cover having a caliber of 5~15 cm and a height of 4~10 cm is formed (see FIG. 4b), and can support breast prosthesis at sizes between 125 cc and 1250 cc.

A specific design of at least five petals can also be used in embodiments of the invention, and is more precise to fit the breast prosthesis, but the difficulty of the production thereof would increase accordingly.

Figure 5:
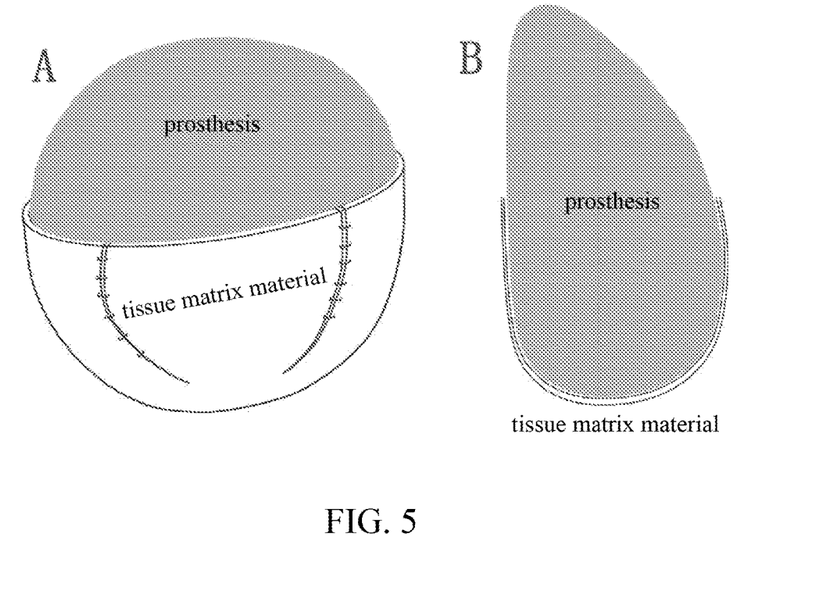
FIG. 5 is an application diagram of the support device for breast prosthesis based on the tissue matrix. (A) a front view after supporting, fixing and covering the breast prosthesis according to the design of the support device for breast prosthesis of embodiments of the present invention; (B) a lateral view after supporting, fixing and covering the breast prosthesis according to the design of the support device for breast prosthesis of embodiments of the present invention.

In various surgical operations such as breast reconstruction, mammoplasty and breast orthopedics, such bowl-shaped or cup-shaped biological tissue device may be fixed at a desired position, and the breast prosthesis is then placed within the bowl cover or cup cover, where the device functions as the support and the cover for the breast prosthesis (see FIG. 5) and makes the breast reconstruction having the desirable projection, thereby achieving better aesthetic and cosmetic effects. Once being implanted, the biological tissue device can be integrated with the surrounding breast tissue and remodeled into new tissues in the human body as the tissue matrix is gradually resorbed without the retention of foreign bodies.

In some breast reconstructions and plastic surgeries, complications may occur that include malposition, malformation, poor coverage, wrinkling, capsule formation and its contraction and the like. The support device for breast prosthesis of embodiments, of the present invention can be used to treat these complications occurring after breast augmentation. For example, the biological tissue device having bowl-shaped or cup-shaped curved surfaces of embodiments of the present invention can be used to manage the size and position of the implant pocket in front of the chest, as if an internal bra being implanted into the body, in order to better support and maintain the position of the breast prosthesis, thereby reducing the relaxation of the autologous tissues of the patients caused by pressure and tension.

A membranaceous acellular tissue material for manufacturing the device of embodiments of the present invention can be a matrix material produced by a series of steps of decellularization, virus inactivation and sterilization from a raw material of a skin tissue, small intestine submucosa, diaphragm, muscle tendon or bladder and the like from donated human cadavers. Also, it can be a matrix material produced by a series of steps of decellularization, immunogenicity reduction, virus inactivation and sterilization using a raw material of a skin tissue, small intestine submucosa, diaphragm, muscle tendon or bladder and the like from pig, bovine, horse or any nonhuman mammal.

The membranaceous acellular tissue material for manufacturing the device of embodiments of the present invention can further be produced from a membranaceous material reconstructed from homogenized acellular tissue material and/or extracted collagen. Wherein, before or after homogenization and extraction, the acellular tissue material can be virus inactivated and sterilized.

Example 1

Fresh pericardium was collected from a newly slaughtered bovine. After the attached adipose tissue being stripped manually, the fresh pericardium was temporarily stored in a 0.9% sodium chloride solution and kept in a refrigerator at 4° C. overnight. After being washed in ultrasonic water bath for 30 minutes, the thickness of the pericardium was measured as 0.4~0.7 mm. Each of 100 g of the pericardium material was decellularized with 1 L of 2% sodium deoxycholate solution (which was dissolved in a buffer solution of hydroxyethylpiperazine-ethanesulfonic acid containing 10 mM ethylenediamine tetraacetic acid, with the pH of 7.4), and shaked and washed in a rotary shaker for 16 hours. The decellularized pericardium was placed in 1 N sodium hydroxide solution to be treated for one hour. The pH was adjusted to be neutral with 10 N hydrochloric acid. Then, it was treated with a 12% sterile sodium chloride solution for 6 hours, and washed with a 0.9% sterile sodium chloride solution for 4 times, each time for 8 hours. The thickness of the pericardium was increased after treatment. The decellularized pericardium is temporarily kept in a refrigerator at 4° C.

Example 2

The decellularized bovine pericardium having a thickness of 0.6~0.9 mm, a length of 20 cm, and a width of 16 cm was used. The pericardium was tailored into petals with two kinds of different sizes and shapes as shown in FIG. 3a, in which two petals have a width of 9 cm and a height of 7 cm, and the other two petals have a width of 7 cm and a height of 9 cm. 16 holes having a diameter of 3 mm were perforated in a region where the four petals were connected to each other, with a space between the holes of 1 cm. After the adjacent convex edges between the petals being stitched with polypropylene sutures together, a flat bowl cover or cup cover of a biological tissue having a caliber of about 9 cm and a height of about 7 cm was formed (see FIG. 3b). Once being stitched, it was washed with 0.9% sodium chloride solution; and then was sterilized using 25 kGy gamma ray after being packaged. The device can support breast prosthesis at sizes between 250 cc and 450 cc, and cover about 180 square centimeters of the surface of the breast prosthesis.

Example 3

Fresh porcine hide was collected from a newly slaughtered pig, and after the hide being dehaired manually, the porcine dermis, having a thickness of about 0.8 mm, was separated and cryopreserved at −20° C. After the dermis being thawed, it was soaked in a saline solution containing 100 mg of gentamicin per liter for 4 hours. The porcine dermis was transferred into 0.5% Triton X-100 solution to be decellularized for 20 hours. Then, after being decellularized and washed, it was firstly rinsed with normal saline twice, each time for 120 minutes. After being washed, it was sterilized and virus inactivated with 0.2% peroxyacetic acid for 4 hours. Finally, it was rinsed with a sterile normal saline until no Triton X-100 remained. The thickness of the treated derm was increased by about 20%. The treated dermal matrix was temporarily kept in 0.9% sodium chloride solution.

Example 4

A decellularized porcine dermis having a length of 16 cm, a width of 16 cm, and a thickness of 0.9~1.1 mm was used. It was tailored into three petals having a width of 9 cm and a height of 7 cm as shown in FIG. 2a. 16 holes having a diameter of 3 mm were perforated in a region where the three petals were connected to each other, with a space between the holes of 1 cm. After the adjacent convex edges between three petals being stitched with polypropylene sutures together, a flat bowl cover or cup cover of a biological tissue having a caliber of about 9 cm and a height of 5 cm was formed (see FIG. 2b). Once being stitched, it was washed with 0.9% sodium chloride solution; and then was sterilized using 25 kGy gamma ray after being packaged. The device can support breast prosthesis at sizes between 250 cc and 350 cc, and cover about 150 square centimeters of the surface of the breast prosthesis.

It should be noted that the above description merely illustrates preferable examples of the present invention, rather than hereby limits the protection scope of the present invention, and the above technical solutions of the present invention may be improved, or replaced with technical equivalents. Therefore, the equivalent structure variations made by using the content of the specification and the drawings of the present invention, and its direct or indirect applications in the other related technical field are encompassed in the scope defined by the present invention.

What we claim is:

1. A support device for breast prosthesis based on a tissue matrix material, the device comprising a petal-shaped planar biological matrix blank tailored from a membranaceous biological planar material, wherein adjacent edges of the petal-shaped planar biological matrix blank are connected to form the support device for breast prosthesis, wherein the petal-shaped planar biological matrix blanks comprise at least one drainage hole.

2. The support device for breast prosthesis according to claim 1, wherein the membranaceous biological planar material is an acellular tissue material, or wherein the number of the petal-shaped planar biological matrix blanks is 2-5.

3. The support device for breast prosthesis according to claim 1, wherein the support device for breast prosthesis has bowl-shaped or cup-shaped curved surfaces.

4. The support device for breast prosthesis according to claim 1, wherein the at least one drainage hole is positioned in the middle of the connected petal-shaped planar biological matrix blanks.

5. The support device for breast prosthesis according to claim 1, wherein the at least one drainage hole is of a single rounded, square, rectangular or triangular shape, or a combination of a plurality of different shapes.

6. The support device for breast prosthesis according to claim 1, wherein each of the petal-shaped planar biological matrix blanks has three convex edges.

7. The support device for breast prosthesis according to claim 6, wherein a support device having bowl-shaped or cup-shaped curved surfaces is formed by stitching, adhering, laser-welding or radiofrequency-welding of the adjacent convex edges of two adjacent petal-shaped planar biological matrix blanks together.

8. The support device for breast prosthesis according to claim 1, wherein the membranaceous biological planar material has a length of 10 cm to 25 cm, and a width of 6 cm to 25 cm.

9. The support device for breast prosthesis according to claim 1, wherein the pore size of the at least one drainage hole is 2 mm to 6 mm.

10. A method for manufacturing the support device for breast prosthesis based on the tissue matrix material according to claim 1, comprising the steps of:
  (a) providing a skin tissue, small intestine submucosa, diaphragm, muscle tendon or bladder as a raw material, which is harvested from a donated human cadaver or from animals;
  (b) performing the decellularization, virus inactivation and sterilization of the raw material in step (a), to produce a membranaceous planar matrix material; or reconstructing from the homogenized acellular tissue material and/or extracted collagen after performing the decellularization, virus inactivation and sterilization of the raw material in step (a), to form a membranaceous planar matrix material;

(c) tailoring the membranaceous planar matrix material obtained from step (b) to form a petal-shaped planar biological matrix blank, wherein the petal-shaped planar biological matrix blanks comprise at least one drainage hole;

(d) connecting adjacent edges of the two petal-shaped planar biological matrix blank in step (c) to form the support device for breast prosthesis.

11. The method according to claim 10, wherein the number of the petal-shaped planar biological matrix blanks is 2-5.

12. The method according to claim 10, wherein the support device for breast prosthesis has bowl-shaped or cup-shaped curved surfaces.

13. The method according to claim 10, wherein the at least one drainage hole is positioned in the middle of the connected petal-shaped planar biological matrix blanks.

14. The method according to claim 10, wherein the at least one drainage hole is of a single rounded, square, rectangular or triangular shape, or a combination of a plurality of shapes.

15. The method according to claim 10, wherein each of the petal-shaped planar biological matrix blanks has three convex edges.

16. The method according to claim 15, wherein a support device having bowl-shaped or cup-shaped curved surfaces is formed by stitching, adhering, laser-welding or radiofrequency-welding of the adjacent convex edges of two adjacent petal-shaped planar biological matrix blanks together.

17. The method according to claim 10, wherein the membranaceous biological planar material has a length of 10 cm to 25 cm, and a width of 6 cm to 25 cm.

18. The method according to claim 10, wherein the pore size of the at least one drainage hole is 2 mm to 6 mm.

* * * * *